United States Patent
Park

(10) Patent No.: US 7,020,325 B2
(45) Date of Patent: Mar. 28, 2006

(54) 3-DIMENSION SCANNING SYSTEM FOR COMPUTER-AIDED TOOTH MODELLING AND METHOD THEREOF

(75) Inventor: Kang Park, Seongnam-si (KR)

(73) Assignee: KCI Co., Ltd., Seoul (KR)

( * ) Notice: Subject to any disclaimer, the term of this patent is extended or adjusted under 35 U.S.C. 154(b) by 667 days.

(21) Appl. No.: 10/148,924

(22) PCT Filed: Oct. 6, 2001

(86) PCT No.: PCT/KR01/01674

§ 371 (c)(1),
(2), (4) Date: Jun. 5, 2002

(87) PCT Pub. No.: WO02/30318

PCT Pub. Date: Apr. 18, 2002

(65) Prior Publication Data

US 2003/0068079 A1    Apr. 10, 2003

(30) Foreign Application Priority Data

Oct. 7, 2000    (KR) .............................. 2000-59071

(51) Int. Cl.
*G06K 9/00* (2006.01)
(52) U.S. Cl. ...................... 382/154; 382/285; 345/419; 356/12; 348/42; 359/462; 433/213
(58) Field of Classification Search ................ 382/154, 382/285; 345/419–427; 356/12–14; 348/42–60; 359/462–477; 352/57–65; 33/20.4; 353/7–9; 396/324–331; 433/49, 213

See application file for complete search history.

(56) References Cited

U.S. PATENT DOCUMENTS

| | | | | |
|---|---|---|---|---|
| 5,071,252 A | * | 12/1991 | Matsuura | 356/601 |
| 5,078,599 A | * | 1/1992 | Eenboom et al. | 433/29 |
| 5,124,524 A | * | 6/1992 | Schuster et al. | 219/121.78 |
| 5,198,877 A | * | 3/1993 | Schulz | 356/614 |
| 5,257,203 A | * | 10/1993 | Riley et al. | 700/163 |
| 5,338,198 A | * | 8/1994 | Wu et al. | 433/213 |
| 5,452,219 A | * | 9/1995 | Dehoff et al. | 700/163 |
| 5,549,476 A | * | 8/1996 | Stern | 433/223 |
| 5,605,459 A | * | 2/1997 | Kuroda et al. | 433/214 |
| 6,200,135 B1 | * | 3/2001 | Hultgren | 433/49 |
| 2001/0002310 A1 | * | 5/2001 | Chishti et al. | 433/24 |

* cited by examiner

*Primary Examiner*—Bhavesh M. Mehta
*Assistant Examiner*—Aaron Carter
(74) *Attorney, Agent, or Firm*—Rosenberg, Klein & Lee

(57) ABSTRACT

Disclosed is a 3-dimension (3D) scanning system for a computer-aided tooth modeling capable of extracting a configuration of a tooth into a 3D configuration data in a short time. The 3D scanning system includes an image detecting part for extracting an image data of a tooth plaster model, a moving part for changing a location and a position of the tooth plaster model measured by the image detecting part, and a control part for changing and controlling the location and the position of the tooth plaster model by controlling the moving part to measure the tooth plaster model using the image detecting part.

5 Claims, 10 Drawing Sheets

3-DIMENSION SCANNING SYSTEM FOR COMPUTER-AIDED TOOTH MODELLING AND METHOD THEREOF

TECHNICAL FIELD

The present invention relates to a 3-dimension scanning system for a computer-aided tooth modeling and a method thereof, and more particularly, to a 3-dimension scanning system for a computer-aided tooth modeling and a method thereof which can extract a tooth configuration into a 3-dimension configuration data in a short time.

BACKGROUND ART

In general, an orthodontic treatment for correcting a tooth carried out in a dental clinic is a series of procedures of dealing with prevention and correction of functional disorder caused due to irregularities of the teeth-generally entailing the straightening of crooked tooth or the correcting of a poor bite, or malocclusion (physiologically unacceptable contact of opposing dentition) and of esthetic disorder generally entailing the correcting of a protruding chin, a snaggletooth, an inturned tooth, or the likes.

The correcting treatment includes the steps of manufacturing a plaster cast of a patient's teeth at a point of initializing the treatment and measuring a configuration data, such as a location of the tooth, a gradient of the tooth, and the likes, determining a proper method for correcting the irregular teeth into regular teeth, and mounting a bracket for correction. However, the conventional method has a drawback in measuring the configuration data since the 3-dimension (3D) configuration data including the tooth location and gradient are manually measured, thereby deteriorating accuracy and consuming lots of time and labor. In addition, the conventional method requires a large storage space and careful maintenance since a lot of plaster casts should be stored until the correcting treatment finishes.

To solve the aforesaid problems, there is suggested a 3D scanning system which can 3D scan a plaster model for a computer modeling, extract a 3D configuration data on a computer, and store the plaster model in a computer data form.

In contrast to the conventional method in which the tooth plaster model is manually measured for dental correction, the 3D scanning system uses a 3D-coordinate measuring system in a manner that a plaster model is analyzed and data is processed in a computer, so that the configuration data necessary for the dental correction can be exactly measured in a shorter time.

For this, it is required a technology, which is capable of accurately measuring the plaster model and enabling a real value to become the same as a measured value, such as acquisition of image, removal of error and noise and conversion of data, and a surface generation technology, namely a mesh and a curved surface generation technology, which is capable of generating a surface of an object by using a point data to measure the configuration data of the tooth model using a 3D point data obtained by the measurement.

The configuration created on the computer in this manner is useful for many fields in next studies as well as dental correction. Meanwhile, the tooth plaster model which becomes the object to be measured for the dental correction is very complex in shape and very rough on surface thereof. In addition, the plaster model is almost uniform in its overall shape and size and uniform in its quality and color. In measuring the tooth plaster model having the aforementioned characteristics, there are parts which are important to the orthodontic treatment and other parts which are not important. It is desirable that a measuring time is the shortest possible and input of dentists is minimized until a result is obtained.

Further, as for the measurement result, a measure accuracy is high enough to be used for medical treatment purpose, locations and intervals of measurement points are selectable to generate the tooth model in computer graphics, and the configuration data for medical use is extracted from the measurement points.

An existing 3D scanner is divided into a non-contact 3D scanner and a contact 3D scanner. The existing 3D scanner has the following features and problems in measuring the tooth plaster model having the above characteristics.

1. Non-contact 3D Scanner

The non-contact 3D scanner is classified into a scanner which linearly drives a laser distance sensor in three directions, and a scanner which uses a laser slit and a camera. The 3D scanner using the laser distance sensor is difficult to measure a vertical plane or a surface which fronts to the bottom. Therefore, a physical position of the object should be changed, the origin should be defined again and the object should be measured again, such that a measuring time is extended and a skillful technology is required. Further, a Z-axis should be moved along the shape of the object and an expensive reverse engineering program is required to extract the configuration data necessary for the orthodontic treatment.

The scanner using the laser slit and camera is capable of performing a linear movement of one degree of freedom. However, this scanner disadvantageously generates a portion which is not able to be measured since when an object has a complex shape, a range of vision of the camera is hidden by the shape of the object itself, and the scanner requires the expensive reverse engineering program to extract the configuration data necessary for the orthodontic treatment.

2. Contact 3D Scanner

The contact 3D scanner obtains a 3D coordinate of a contact point by linearly moving a probe in three directions and contacting the same to an object. This scanner can't measure a curvature more minute than the probe in size and has a difficulty in measuring a downward-facing surface. When measuring the downward-facing surface, the scanner changes a position of the object, defines the origin again, measures the object again. Accordingly, an operator should move the probe in person to measure the downward-facing surface, thereby extending a measuring time and requiring a skillful technology. Additionally, the equipment is high priced and the expensive reverse engineering program should be used to extract the configuration data for the medical purpose.

As stated above, both the conventional non-contact and contact 3D scanners for measuring the tooth plaster model have drawbacks in that the complex-shaped model is difficult to be measured, the skillful measuring technology is required and the expensive reverse engineering program is required to extract the configuration data.

DISCLOSURE OF INVENTION

Accordingly, the present invention is directed to a 3D scanning system for a computer-aided tooth modeling and a method thereof that substantially obviates one or more problems due to limitations and disadvantages of the related art.

An object of the present invention is to provide a 3D scanning system for a computer-aided tooth modeling and a method thereof which can generate a computer model without a separate reverse engineering program by 3D scanning a tooth plaster model.

Another object of the present invention is to provide a 3D scanning system for a computer-aided tooth modeling and a method thereof which can improve reliability in a tooth configuration data without an operator's skillful technology by minimizing a portion which cannot be measured without the operator's handling when a complex-shaped tooth plaster model is measured.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, there is provided a 3D scanning system for a computer-aided tooth modeling, the scanning system comprising: image detecting means for extracting a configuration data of a tooth plaster model; moving means for changing a location and a position of the tooth plaster model measured by the image detecting means; and control means for changing and controlling the location and the position of the tooth plaster model by controlling the moving means to measure the tooth plaster model by means of the image detecting means.

The image detecting means comprises a laser for emitting a laser beam to the plaster model which is an object to be measured; a camera for picking up a reflected beam emitted by the laser; and a video board for grabbing an image signal picked by the camera. The moving means comprises a turn table for allowing the tooth plaster model to be mounted thereon and being rotated and tilted to change the position of the tooth plaster model; rotating means for rotating the turn table; a tilting means for tilting the turn table; and linear moving means for linearly moving the turn table.

The control means measures the object by using an automatic teaching method, which comprises the steps of: simulating a 3D configuration measuring device on a virtual space; generating a mesh with respect to a reference tooth model; setting a tooth to be measured; building a reasoning algorithm to automatically determine a measurement angle and a measurement location for the purpose of precisely measuring teeth having different shape and size; incorporating a real measurement result into a database to obtain an accurate measurement path; determining a measurement position including the measurement angle and the measurement location through the reasoning process of database; measuring the tooth model by using the measurement position and the measurement path determined in the above steps; checking whether there exists a portion where the tooth model is not measured, changing the position if the unmeasured portion exists, and measuring the tooth model again, and adding the result to the database. The control means extracts a configuration data for dental correction by performing the steps of: calculating a 3D coordinate of the tooth configuration, expressing the data into a mesh according to needs and displaying a surface of the tooth; extracting a curved surface data by using the mesh; and extracting the configuration data by using the curved surface data.

The present invention provides also provides a 3D scanning method for a computer-aided tooth modeling, the scanning method comprising the steps of: (a) installing a tooth model on a base having at least 3-axis rotational degree of freedom, determining an order of scanning a surface of the tooth model and simulating a position where a cross section of a laser emitted onto the surface is minimized; emitting the laser to the tooth model, and scanning and obtaining an image of a laser line; (c) converting the image of the laser line into a gray level image and binarizing the same; (d) finding a center line of the laser line and obtaining a coordinate of the center line; (e) calculating a 3D coordinate by using the center line coordinate and a location of the base; (f) changing the position of the tooth model by changing the location of the base; (g) obtaining a 3D coordinate with respect to an overall surface of the tooth model by repeating the steps from (b) to (f).

As aforesaid, the present invention actively changes the location and the position of the tooth plaster model when 3D scanning the tooth plaster model for dental correction, so that the measurement can be accurately and simply performed with respect to most necessary locations without correcting the position.

It is to be understood that both the foregoing general description and the following detailed description of the present invention are exemplary and explanatory and are intended to provide further explanation of the invention as claimed.

BRIEF DESCRIPTION OF THE DRAWINGS

Further objects and advantages of the invention can be more fully understood from the following detailed description taken in conjunction with the accompanying drawings, in which.

BEST MODE FOR CARRYING OUT THE INVENTION

Figure 1:
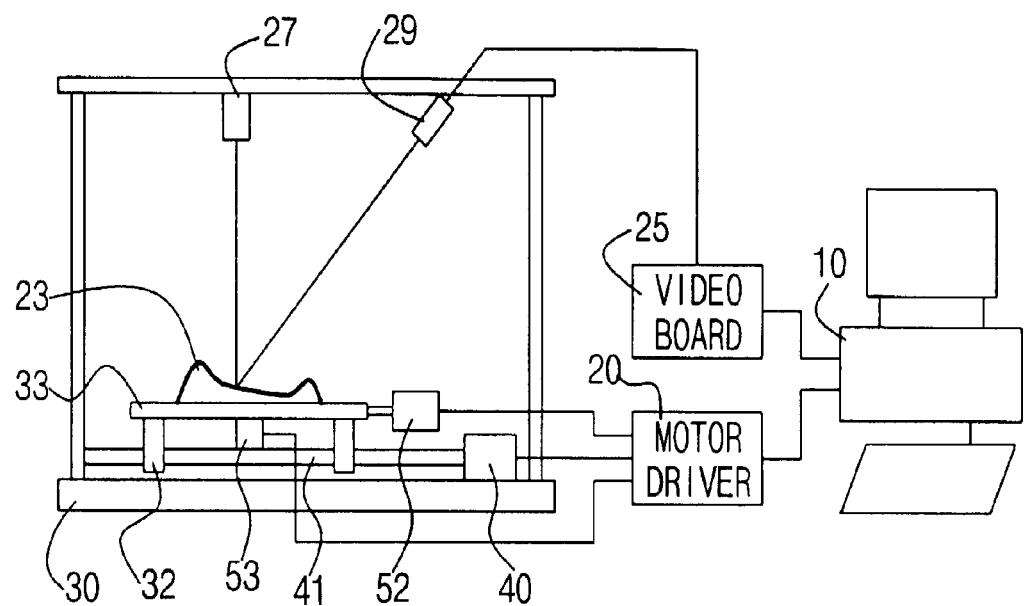
FIG. 1 is a schematic view illustrating a construction of a 3D scanning system for a computer-aided tooth modeling according to the present invention.
Figure 2:
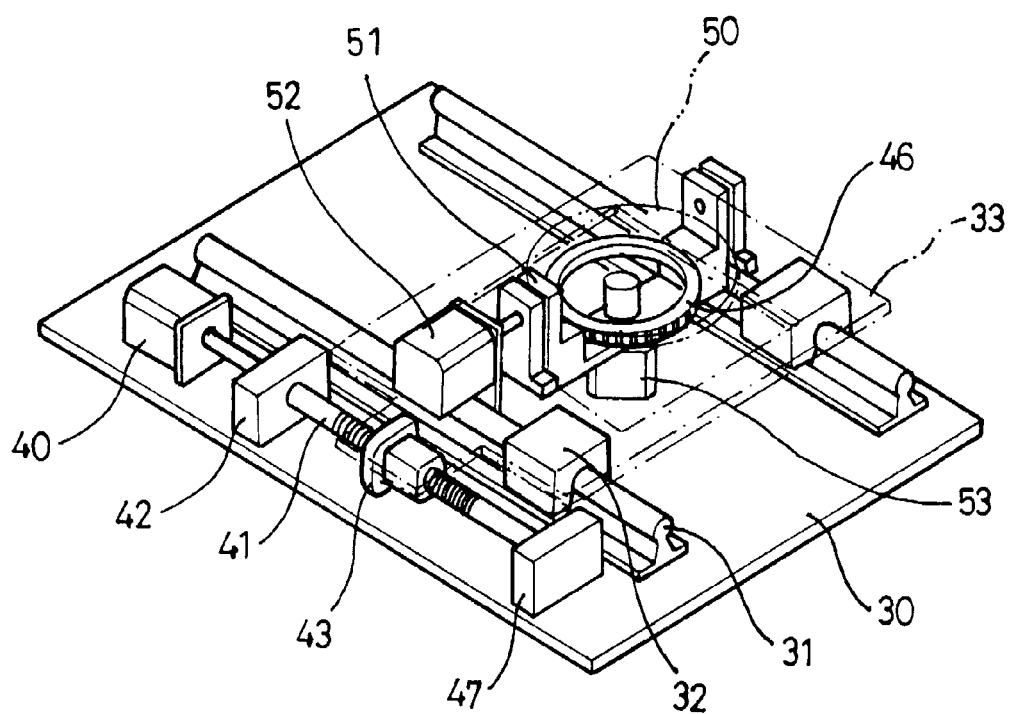
FIG. 2 is a schematic cross view illustrating a construction of a 3D scanning system for a computer-aided tooth modeling according to the present invention.

Reference will now be made in detail to the preferred embodiments of the present invention, examples of which are illustrated in the accompanying drawings.

The present invention relates to a 3D scanning system with regard to a tooth plaster model 23 necessary for dental correction, the scanning system roughly comprising an image detecting part, a moving part and a control part.

The image detecting part includes a laser 27 for emitting a laser beam to the tooth plaster model 23, a camera 29 for picking up a reflected beam which is emitted by the laser 27 and reflected by the tooth plaster model 23, and a video board 25 for grabbing an image signal picked by the camera 29.

The moving part serves to minimize an area which cannot be measured by moving a location of the tooth plaster model 23 or changing a position of the tooth plaster model 23.

The tooth plaster model 23 is put on a turn table 50 which is rotated and tilted to change the location and the position of the tooth plaster mode. The turn table 50 is rotated by a rotating motor 53 which is fixed on a tilting bed 51 attached on a lower surface of the turn table 50.

The tilting bed 51 tilting the turn table 50 makes the turn table 50 possible to be rotated and tilts the turn table 50 rightward and leftward about a central axis. The tilting bed 50 is tilted by a tilting motor 52.

Since the rotary central axis of the turn table is tilted by the tilting bed 51, a portion supporting the central axis of the turn table 50 should be movably supported by a bearing. For this, a movable part movably supports a lower part of the central axis of the turn table 50, thereby enabling a relative rotation between the tilting bed 51 and the turn table 50.

The movable part is installed on a linear transformation bed 33 which is linearly moved. The linear transformation bed 33 is fixed on a slider which is installed on a lower surface of an edge portion of the linear transformation bed 33.

The slider 32 is mounted on a rod 31 which is fixed on a base 30 and linearly movable. A screw nut 43 is mounted on one end of the linear transformation bed 33 and linearly moved by a screw 41 so as to linearly move the linear transformation bed 33.

The screw 41 is rotated by a linear motor 40 and supported by a screw support part 42 on a center thereof. The base 30 is preferably made of a material which is sufficiently weighty for an optical system including the laser 27 and the camera 29 to maintain a stable environment without being effected by an external vibration.

Meantime, the linear motor 40, the rotating motor 53 and the tilting motor 52 are stepping motors, which are driven by a motor driver 20 under a control of the control part.

The control part, as shown in FIG. 1, extracts the configuration data of the tooth plaster model through an image signal inputted through the video board 25 and a control signal of each motor driven by the motor driver 20. The control part uses a PC(Personal Computer).

Figure 4:
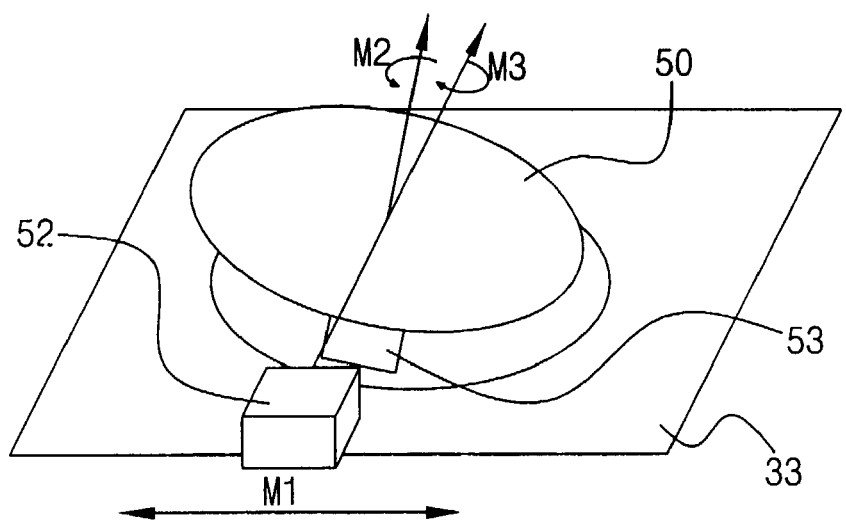
FIG. 4 is a view for explaining location and position change of a turn table according to the present invention.

The linear motor 40, the rotating motor 53 and the tilting motor 52 are stepping motors. In order to constrain an angle of rotation, a limit switch (not shown) is installed on each motor. As for location and position change of the turn table by means of the each motor, as drawn in FIG. 4, the turn table 50 is linearly moved by the linear motor 40 (M1), the turn table 50 is rotated by the rotating motor 53 (M2) and the turn table 50 is tilted by the tilting motor (M3).

The control signal controlling the each motor is a control signal output through a parallel port from the control part 10 and is a square pulse having 0V at Low and 5V at High. The pulses are inputted to the motor driver 20 consecutively through output pins from $2^{nd}$ to $9^{th}$ pin, such that the motor driver 20 divides the pulses and consecutively distribute the pulses to the motors through respective lines of the motors, thereby rotating the motors. The motor rotates one step each pulse and thus a five-phase stepping motor, which provides resolutions as fine as 500 steps per revolution, rotates at 0.72 degrees (360÷500) per pulse.

An input signal of two lines is introduced to one stepping motor, one controlling a direction of the motor and the other controlling an angle of the motor by virtue of the aforementioned pulse. In addition, a signal inputted from the limit switch is inputtable through $12^{th}$, $13^{th}$ and $25^{th}$ pins of the parallel port, thereby making a rotated condition of the each motor possible to be identified.

Figure 3:
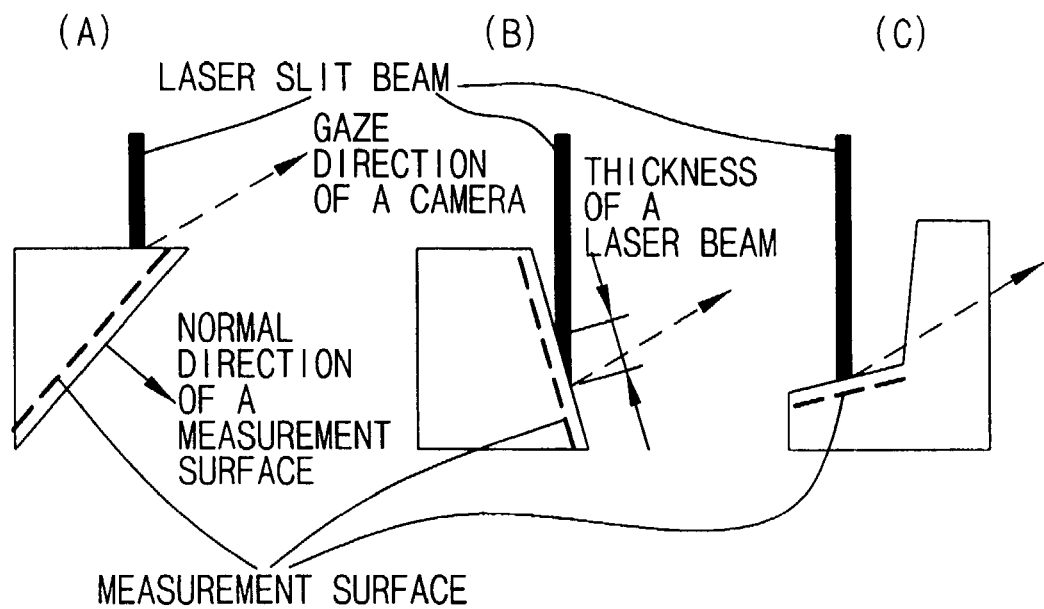
FIG. 3 is a view for explaining an angle at which an object cannot be measured according to a position of the object and an angle of emitting a laser beam in the conventional art.

FIG. 3 is a view for explaining drawbacks of the conventional 3D scanner in measuring the tooth plaster model.

The conventional 3D scanner causes the problems: when the laser does not reach a measurement surface since the measurement surface is downwardly directed in relation to a direction of emitting the laser slit beam as shown in FIG. 3(*a*), when an exact measurement can not be carried out since a gradient between the measurement surface and the laser slit beam is too steep as shown in FIG. 3(*b*), and when the object cannot be seen by the camera since the laser beam emitted to the measurement surface is hidden by other portions of the object as shown in FIG. 3(*c*).

To solve the problems of FIG. 3(*a*) and FIG. 3(*b*), the laser beam should be emitted in a direction almost perpendicular to the measurement surface by turning the measurement surface. To solve the problem of FIG. 3(*c*), the laser beam emitted to the measurement surface should be seen by the camera by turning the object.

For this, the tooth plaster model is fixed on the turn table 50 having two rotational degree of freedom, and the object is measured by driving the rotating motor 53 and the tilting motor 52 and changing the position of the tooth.

To configure a complex-shaped object like the tooth plaster model needs to teach a measurement position through a simulation. The teaching process will be explained with reference to FIG. 5.

It is very difficult to determine the measurement position in connection with the complex-shaped object like the tooth model. A reference model of the measured tooth is modeled in computer graphics by using the 3D scanner. And then, the measurement process is simulated, such that the measurement angle and the measurement order are determined through the rotating motor 53 and the tilting motor 52. That is to say, the tooth plaster model which is regarded as a reference is read through the scanner and modeled on the computer. It is determined which portion is visible and which portion is invisible according to varying gaze directions while the model is being seen on a monitor. As a result, it is found an angle at which the largest area can be seen according to the configuration of the tooth plaster model. Additionally, it is accordingly reduced trials and errors to find the optimum angle in next measurements.

To realize this, an open GL, namely a computer graphics library, which is a library for 3D graphics and modeling and has excellent transplantation characteristic and fast speed is employed to perform the simulation, and an expert system, which approaches a wanted target through a reasoning process on the basis of many facts and variables, is employed to analogize and determine the order of measuring the tooth plaster model with only a simple operation even by a layman.

An automatic teaching system has been developed to improve accuracy, remove any unmeasured portion, and generate the final optimum measurement position path by using both the open GL and the expert system. Here, the measurement position path is a path or a rotation angle capable of obtaining data of the largest portions at one scanning.

Figure 5:
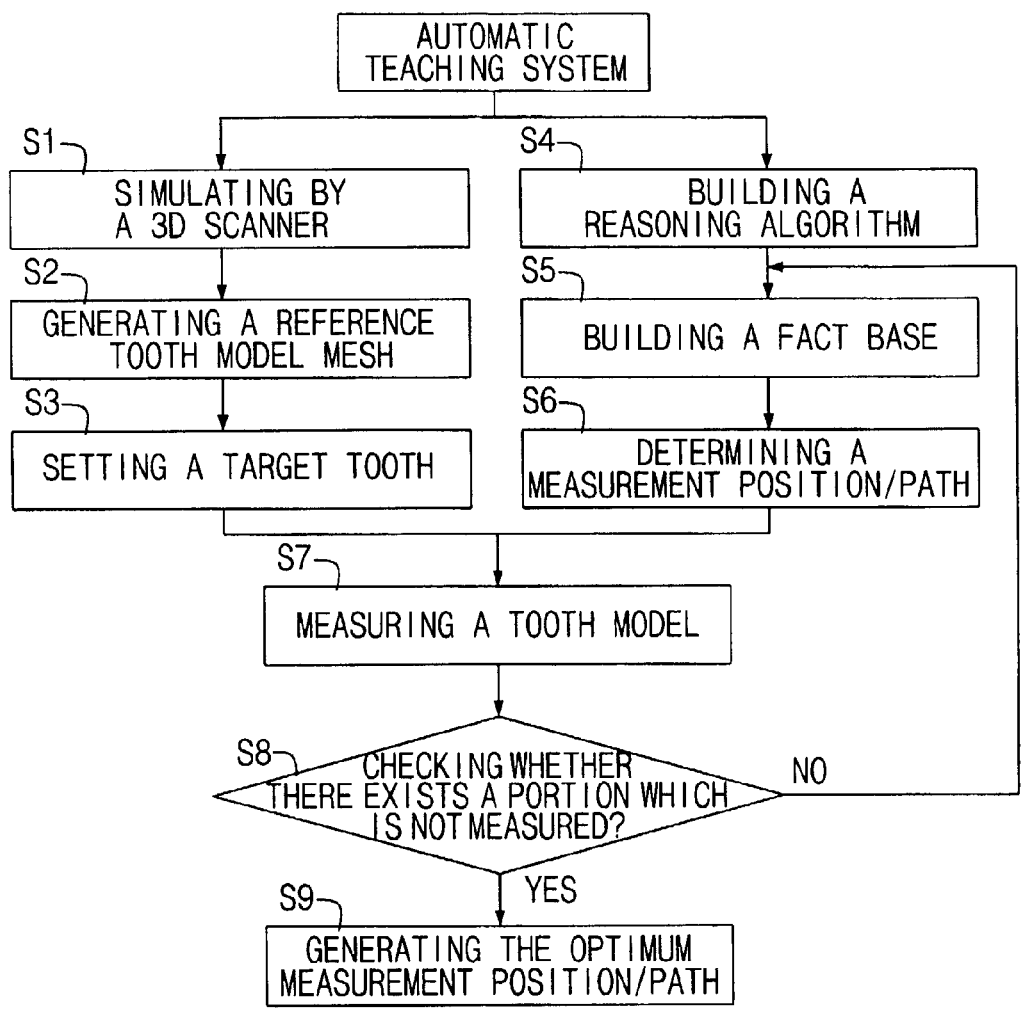
FIG. 5 is a flow chart for explaining an automatic teaching system according to the present invention.

FIG. 5 is a flow chart for explaining the automatic measurement position teaching system. A process of the system will be described hereinafter.

1. Simulating with the 3D scanner open GL(S1)—a completed 3D configuration measuring device is simulated by using the computer graphics open GL.

2. Generating a reference tooth model mesh(S2)—a 3D point data of male and female reference tooth models are generated into a mesh, which is put on the turn table 50 of a virtual 3D scanner. Here, the mesh generation is quite a difficult work since hidden portions or surfaces of an object should be analogized on the computer with only the point data. Therefore, a set of points with respect to a small surface are formed by using the point data and the small surfaces are collected and connected so as to complete an overall outer configuration. Here, one small surface is called one mesh.

3. Setting a target tooth(S3)—since a complex-shaped tooth model is impossible to be measured at once, the tooth model is divided into several parts. A portion of the tooth which becomes a target during the measurement is set as a target tooth. For example, teeth from the center to the third tooth on the left side become the target teeth, which are different depending on sex and age.

4. Building a reasoning algorithm of the expert system (S4)—teeth are different in shape and size depending on sex, age, and existence of a lost or damaged tooth. The reasoning algorithm functions to generate a reasonable result based on facts and rules, so as to automatically determine the measurement angle and the measurement location for the purpose of precisely measuring these various shaped and sized teeth.

5. Building a fact base(S5)—the measurement angle and the measurement location which is different depending on sex, age, and existence of a lost or damaged tooth is incorporated into a database and used as a reference when the expert system analogizes. That is to say, the optimum measurement path is incorporated into a database, wherein the optimum measurement path is obtained through trials and errors according to features of each tooth, for example a front tooth is lost, or a tooth is upwardly protruded. The more number of models are measured, the more accurate path can be attained according to the specific configuration.

Meanwhile, the fact base is formed by putting together facts obtained during the analogizing process and storing intermediate results obtained during the analogizing process or facts answered by users. If a user answers Yes to a question "does it have fur?" in an example for analogizing what is an animal of a zoo, the variable "the animal has fur' and the value "Yes" are stored. A main reason to build the fact base is to prevent the same question from being asked repeatedly to other users by keeping the value obtained during the analogizing process.

6. Determining the measurement position and measurement path(S6)—the measurement position including both the measurement angle and the measurement location is determined through the analogizing process by using the fact base and the measurement path enabling the measurement in the shortest time is determined by combining the measurement position in accordance with each target tooth.

7. Measuring a tooth model(S7)—The tooth model is measured by using the measurement position and the measurement path determined as above.

8. Checking the unmeasured portion(S8)—it is checked whether an unmeasured portion exists after the measuring process. In the affirmative, the position is changed, the tooth model is measured again and the result is added to the fact base.

After a wanted measurement data is obtained through the series of process, the measurement path is determined as the optimum measurement position path. However, if the unmeasured portion doesn't exist, the measurement position and measurement path are automatically determined as the optimum measurement position path. That is, the optimum measurement path becomes a path where the unmeasured portion is minimized.

Figure 6:
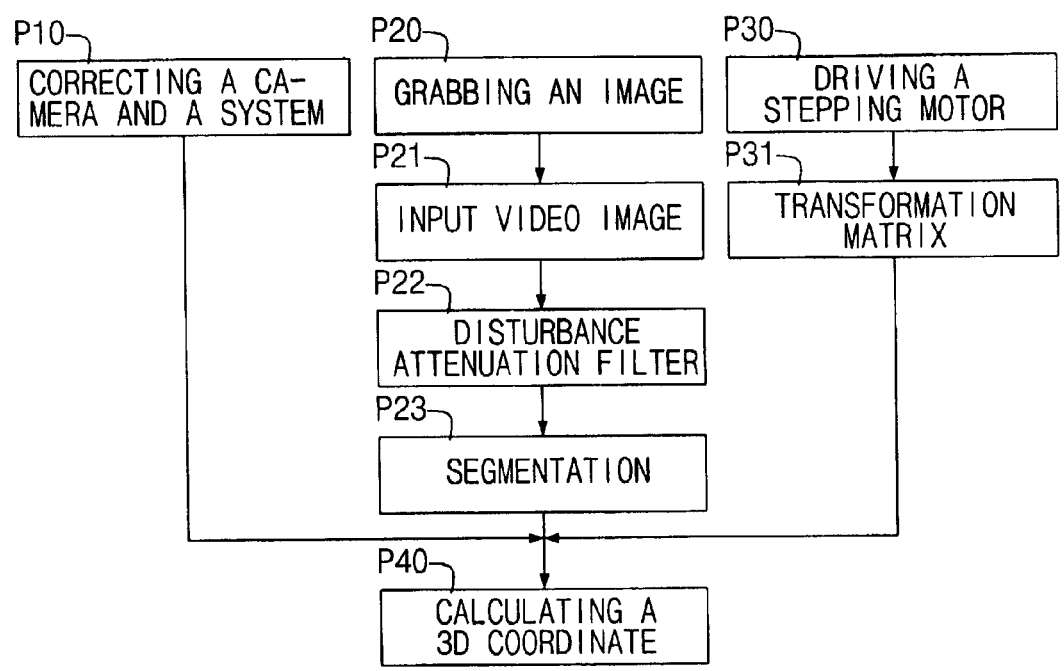
FIG. 6 is a view for explaining a 3D coordinate calculating program.

A process of measuring a 3D coordinate according to the present invention will be explained with reference to FIG. 6.

1. Driving a motor(P30 and P31).

Once the tooth model is fixed on the turn table 50, the coordinate is measured by driving a motor and changing a direction of the tooth. At that time, a conversion matrix is attained by measuring a current motor angle and a configuration of the tooth is measured by automatically converting the measured coordinate into a coordinate relative to a reference coordinate system.

According to the method, the series of process of changing the direction of the object and fixing the object and selecting the origin which are performed in the conventional 3D scanner can be omitted, whereby a measuring time is reduced and a skillful technology does not need.

2. Proessing an image(P20–23, P40)

After the direction of the tooth is determined, a still image is obtained from the video image output from the camera 29 by using the image board(P21). It is possible that the image has a disturbance thereon. A clean image is obtained by using a disturbance attenuation filter(P22). Only a laser slit beam is separated through a segmentation process(P23). At this point, the laser slit beam which is originally linear is distorted due to unevenness of the tooth mode configuration. The distortion is analyzed and the 3D coordinate of the configuration is calculated(P40).

3. Correcting a camera(P10)

In order to use the camera as a measuring equipment, a mathematical model of the camera is precisely corrected and internal correction factors, e.g., as a focal distance, a lens distortion, etc., and external correction factors, e.g., a location of the camera, a position, etc., are exactly obtained to be accorded with values of a real camera.

4. Correcting an overall system(P10).

Error of an overall system is corrected so as to improve final measurement accuracy. The correcting process is performed just one time when the system is completed.

Figure 7:
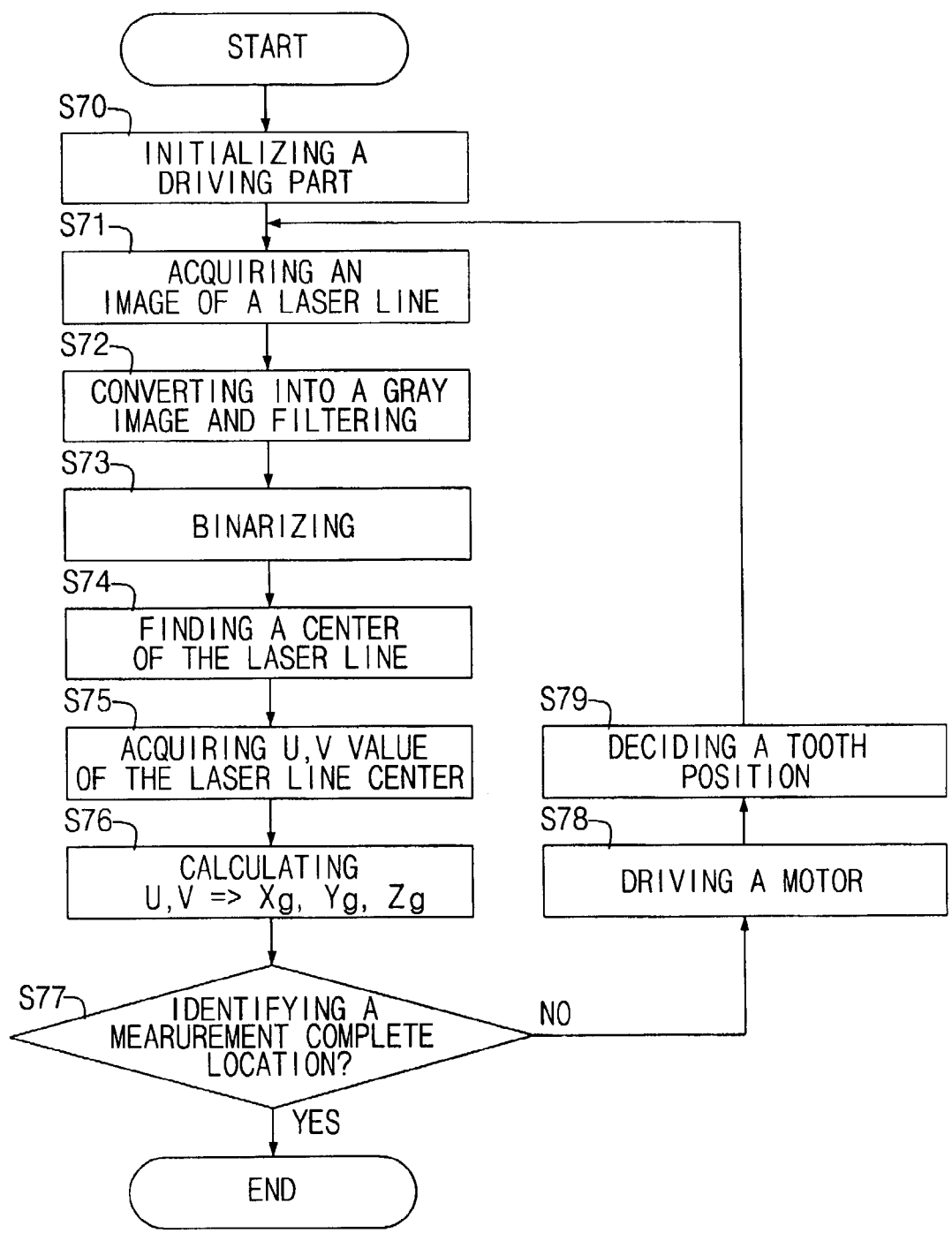
FIG. 7 is a flow chart for explaining an order of measuring a 3D coordinate.

An order of measuring the 3D coordinate of the tooth plaster model 23 according to the present invention will be explained with reference to FIG. 7.

1. Initializing a driving part(S70).

The linear motor 40, the rotating motor 53 and the tilting motor 52 are driven and the turn table 50 is returned to the origin. The turn table is moved to its initial position and at this point, a coordinate of Y-axis, namely a position of the linear transformation bed 33, is stored.

2. Acquiring a laser line image(S71)

When the laser slit beam is emitted to the object, the shape of the slit beam is changed according to the outer shape of the object. The camera 29 receives the image including the laser slit beam generated in the above. Thereafter, the image is stored as a color image of 640*480 through the video board 25.

3. Converting into a gray image and filtering(S72)

Red, green and blue band images of the stored color image are averaged and converted into one gray image.

In case of the image obtained as above, lots of noise is included in a boundary part of the laser slit beam due to laser beam spreading phenomenon. The noise is removed through a mean filtering process which is one of filtering methods. To be specific, an average value of intensity around one point is allotted to the very point so as to remove the noise.

4. Binarizing(S73)

For the purpose of leaving image information concerning only the laser slit beam portion, portions having intensity lower than a predetermined threshold intensity are set to have "0" in intensity.

At this time, a value is determined as the threshold when the image of the laser slit beam portion has the most uniform thickness and the boundary portion of the slit beam has the best smoothness.

5. Finding a center of the laser line and acquiring a coordinate (u, v) on an image plane(S75)

Figure 8:
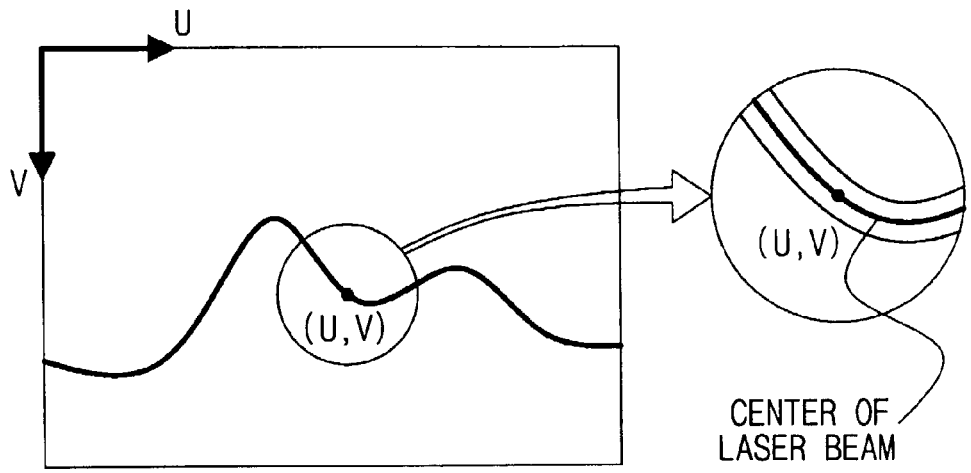
FIG. 8 is a view for explaining an image of a laser slit picked by a camera.

Light intensity distribution in cross section of the laser slit beam picked by the camera 29 is always asymmetric except when an object has a constant gradient. Therefore, the system according to the present invention uses a curve fitting method with regard to the intensity of the slit beam (see FIG. 8 and FIG. 9). This curve fitting method performs a curve fitting by assuming the slit beam as a cubic considering that the light intensity distribution is asymmetric, and obtains a location of the maximum value in the curve.

In this manner, a central value of the slit beam is found in each column of the slit beam image and the central value is stored as a value (u, v) of the image plane coordinate.

Figure 9:
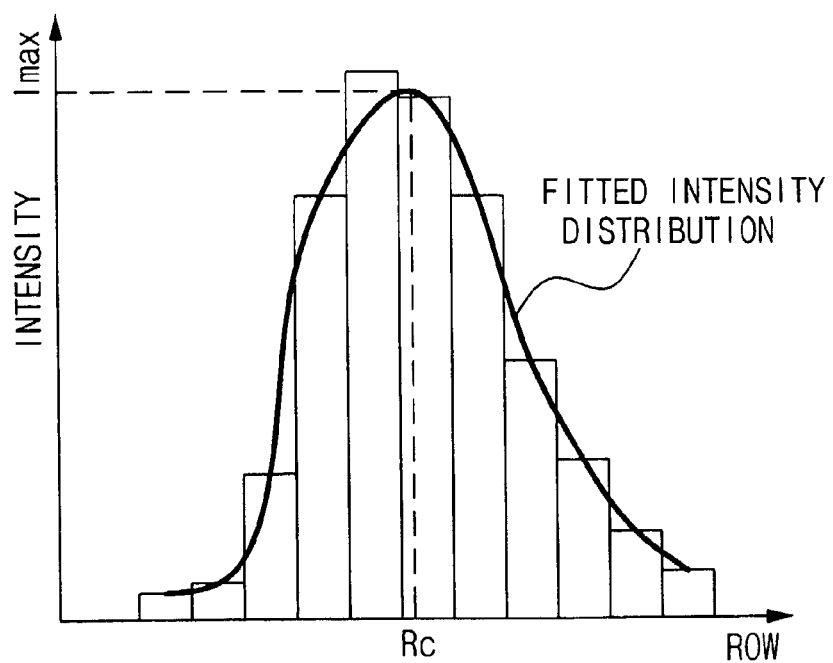
FIG. 9 is a graph for explaining an intensity distribution along a row of the laser slit beam image.

In FIG. 9, Rc signifies a center of the laser slit beam and Imax signifies the maximum intensity of the curve-fitted laser slit beam.

6. Finding a 3D absolute coordinate by using a 2D coordinate on the image plane(S76)

Information concerning a 3D distance in the 3D image picked by the camera 29 is obtained by employing the Ray method which will be described herein below (see FIG. 10).

Figure 10:
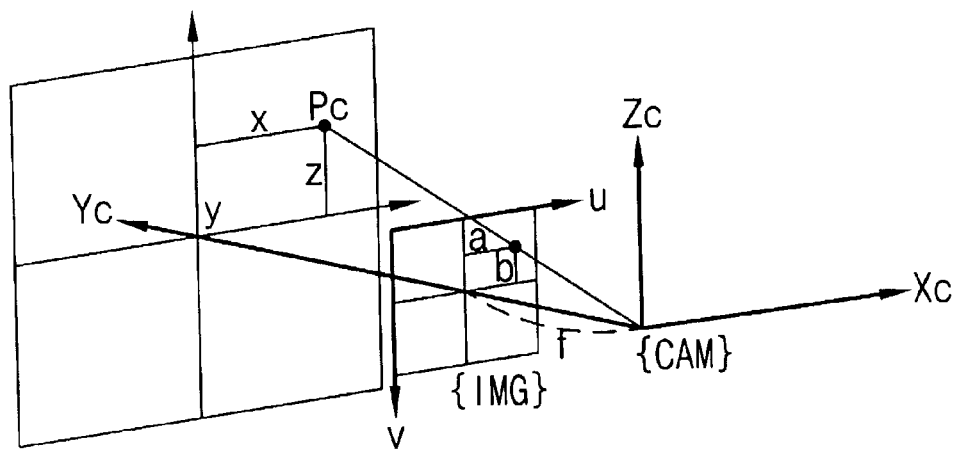
FIG. 10 is a view for explaining a camera coordinate system.

In FIG. 10, CAM is a camera coordinate system(Xc, Yc, Zc), wherein the origin is located on the center of the camera lens, Yc is located in a gaze direction of the camera, Zc is located in an upward direction of the camera and Xc is located in a rightward direction of the camera. IMG is an image coordinate system, which is set on a CCD chip of the real camera and expressed by u, v. $P_c$ is a discretionary point in a 3D space on the bases of the CAM. Uu and Vv are a location in a column and a row of the point $P_c$ projected onto the image coordinate system on the CCD chip of the camera 29. a and b signify coordinate values of Uu and Vv relative to the center of the CCD chip of the camera 29.

Figure 11:
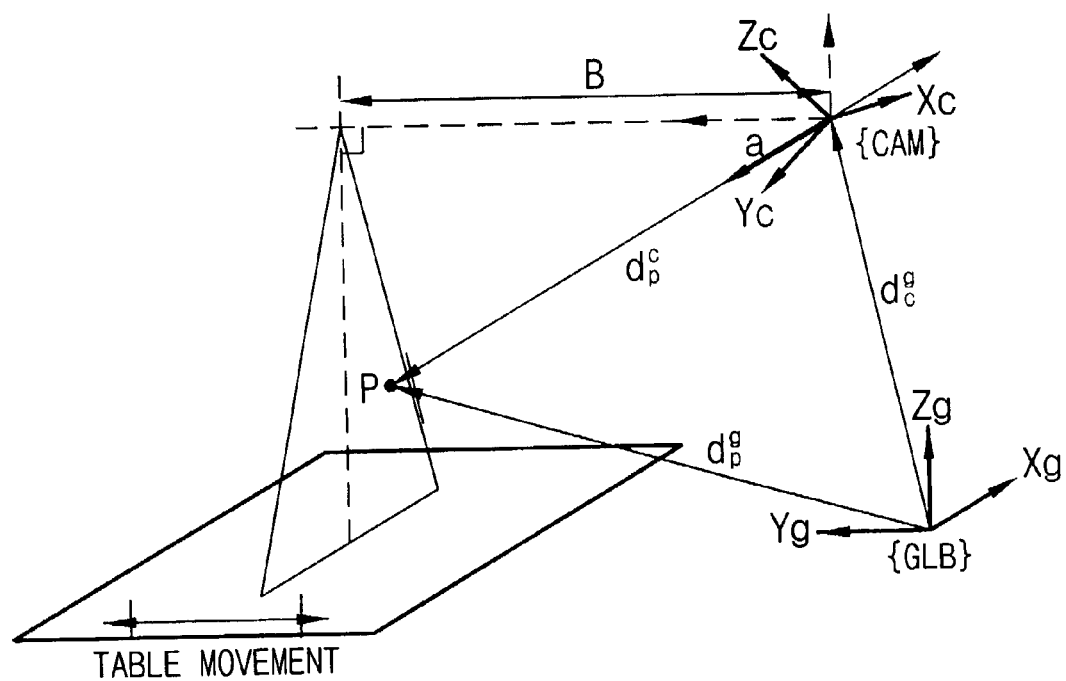
FIG. 11 is a view for explaining a process of calculating coordinate data based on a Ray method.

Referring to FIG. 11, GLB(Global) represents a reference coordinate system which is fixed on the space. CAM represents the camera coordinate system ($X_c$, $Y_c$, $Z_c$). B represents a distance from the origin of the CAM coordinate system toward an $Y_g$-axis up to the laser. P represents a point within the measured laser slit beam. $D_p^c$ represents a vector from the origin of the CAM coordinate system to the point P. a represents a unit direction vector of the $D_p^c$. $D_c^g$ is a vector from the origin of the reference coordinate system to the origin of the camera coordinate system. $D_p^g$ is a vector from the origin of the reference coordinate system to the point P.

(1) In the camera coordinate system defined as above (see FIG. 10), when a coordinate value of the point P relative to the camera coordinate system is $\{d_p^c\}_c = \{X_c, Y_c, Z_c\}_c$, a following equation 1 is calculated, wherein $f_u$, and $f_v$ are respectively a focal distance to u, v directions:

$$u = f_u \frac{x_c}{y_c}, v = -f_v \frac{z_c}{y_c}; \therefore x_c = \frac{u}{f_u} y_c, z_c = -\frac{v}{f_v} y_c \qquad \text{(Equation 1)}$$

Here, the u,v values are obtained in a manner that a real pixel value is read on the image of the point P, and then the u,v values with no lens distortion is calculated by using a lens distortion coefficient of the camera obtained through the camera correcting process. $X_c$ and $Z_c$ in the above equation 1 are expressed in a function of $Y_c$.

(2) A direction vector value $a_c$ from the origin of the camera coordinate system to the point P is obtained by applying yc=1 to calculate $x_c$ and $z_c$, and thereafter a unit vector is formed. The unit vector $a_c$ of P relative to the CAM is obtained by using the following equation 2:

$$a_c = \begin{bmatrix} u \\ v \\ w \end{bmatrix}_c = \frac{1}{den} \begin{bmatrix} x_c \\ 1 \\ -z_c \end{bmatrix}; den = \sqrt{x_c^2 + y_c^2 + z_c^2} \qquad \text{(Equation 2)}$$

(3) $a_c$ expressed by the camera coordinate system is converted into ag expressed by the reference coordinate system by using the equation 3. For this, "a rotation matrix $(ORT)_g^c$ of the camera coordinate system relative to the reference coordinate system" obtained during the process of correcting $a_c$ is multiplied:

$$a_g = \begin{bmatrix} u \\ v \\ w \end{bmatrix}_g = (ROT)_c^g * \begin{bmatrix} u \\ v \\ w \end{bmatrix}_g \qquad \text{(Equation 3)}$$

(4) If it is known the unit direction vector from the origin of the camera coordinate system expressed by the reference coordinate system to the point P, and it is known the distance B between the origin of the camera coordinate system and the laser beam, a coordinate of $\{d_p^c\}_g = \{x_p^c, y_p^c, z_p^c\}_g$ relative to the reference coordinate system can be obtained through the following process.

i) the vector coordinate $\{d_p^c\}_g = \{x_p^c, y_p^c, z_p^c\}_g$ from the origin of the camera coordinate system to the point P and the unit direction vector $a_g$ are identical in direction. Thus, the following equation 4 is given:

$$ka_g = \{d_b^c\}_g \therefore k \begin{bmatrix} u \\ v \\ w \end{bmatrix}_g = \begin{bmatrix} x_b^c \\ y_b^c \\ x_b^c \end{bmatrix}_g \qquad \text{(Equation 4)}$$

where k is a real number.

ii) Here, since the yg direction coordinate value of P relative to the reference coordinate system is B, B is applied to yg as shown in the following equation 5:

$$\{y_P^c\}_g = B \qquad \text{(Equation 5)}$$

$x_g$, $x_g$ values are obtained by using the following equations 6 and 7:

$$ku_g \cdot \{x_p^c\}_g = ku_g \cdot B$$

$$kw_g \cdot \{z_p^c\}_g = kw_g \cdot B \qquad \text{(Equation 6)}$$

$$\{x_p^c\}_g = \frac{u_g}{v_g} * B \qquad \text{(Equation 7)}$$

$$\{z_p^c\}_g = \frac{w_g}{v_g} * B$$

Thus, $\{d_p^c\}_g$ is calculated by the following equation $$\{d_p^c\}_g = \begin{pmatrix} \frac{u_g}{v_g} * B \\ B \\ \frac{w_g}{v_g} * B \end{pmatrix} \qquad \text{(Equation 8)}$$

Finally, the coordinate value $P_g$, or $\{d_p^g\}_g$ is $\{d_p^c\}_g + \{d_c^g\}_g$, and expressed as shown in the following equation 9. Here, $\{d_c^g\}_g$ is obtained through the camera correcting process $$P_g = \begin{bmatrix} x_g \\ y_g \\ z_g \end{bmatrix} = \begin{pmatrix} \frac{u_g}{v_g} * B \\ B \\ \frac{w_g}{v_g} * B \end{pmatrix} = \begin{bmatrix} x_c^g \\ y_c^g \\ z_c^g \end{bmatrix} = \begin{pmatrix} \frac{u_g}{v_g} B + x_c^g \\ B + y_c^g \\ \frac{w_g}{v_g} B + Z_c^g \end{pmatrix} \qquad \text{(Equation 9)}$$

where $x_c^g$, $y_c^g$, $z_c^g$ are the location of the origin of the camera coordinate system relative to the reference coordinate system.

The 3D coordinate ($x_g$, $y_g$, $z_g$) of the object can be obtained from the coordinate (u, v) obtained in the 2D object image through the series of process from (1) to (4).

7. Identifying a measurement complete position(S77)

If the linear transformation bed 33 is moved along the direction $Y_g$(Y-axis) of the reference coordinate by as far as a length of the object inputted during program execution, the measurement is stopped.

8. Changing the tooth measurement direction through motor operation(S79)

The rotating motor 53 and the tilting motor are driven to change the measurement position of the tooth plaster model and the linear motor 40 is driven to linearly move the model.

Angles of the motors for changing the tooth measurement position are attained through the tooth measurement simulation process.

Figure 12:
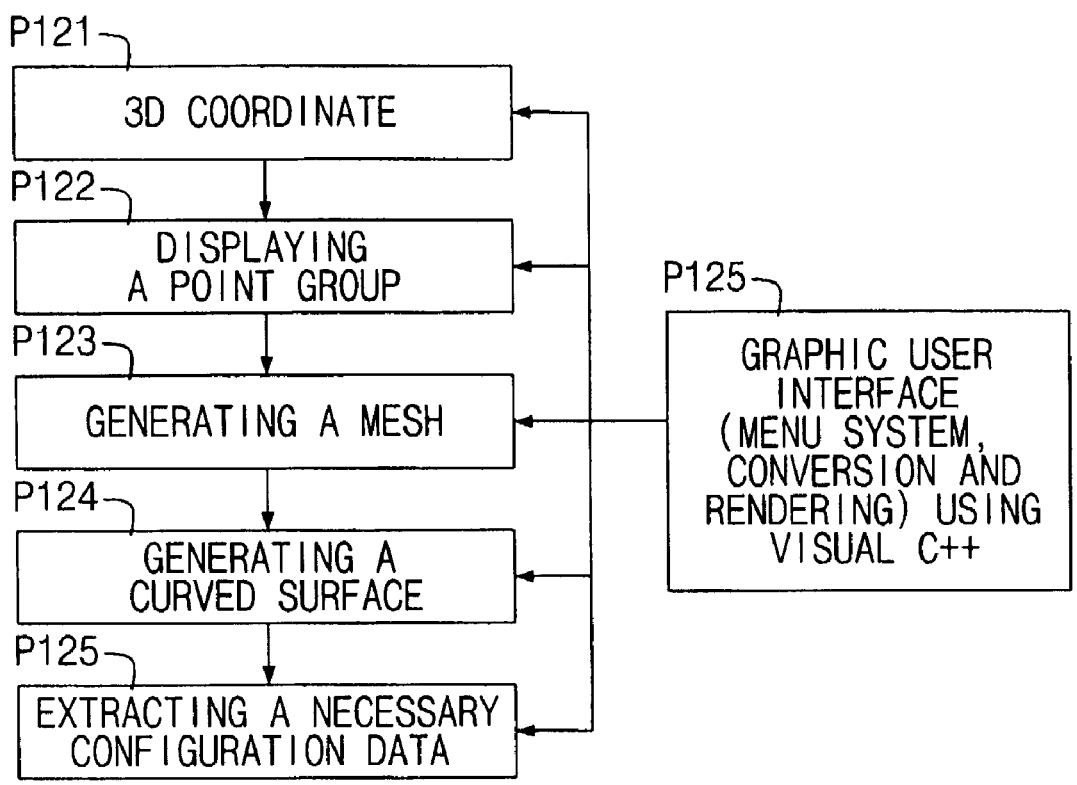
FIG. 12 is a flow chart for explaining a configuration data extracting program.

In the meantime, a process of extracting the configuration data for dental correction will be explained herein blow with reference to FIG. 12.

Figure 13:
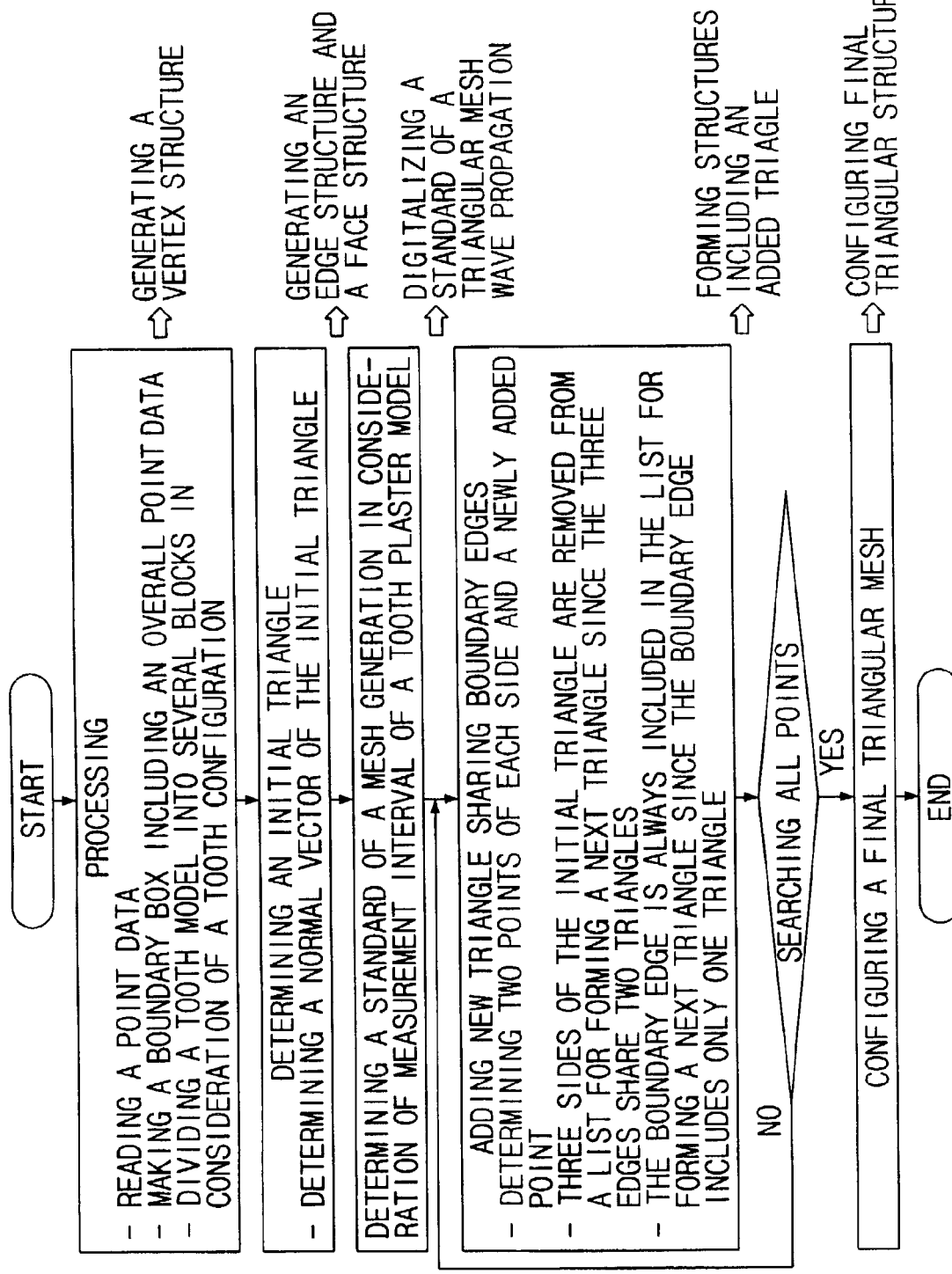
FIG. 13 is a flow chart for explaining a mesh generating algorithm.

1. Generating the mesh (see FIG. 13)

Data obtained by the 3D coordinate has no geometrical and topological information except the coordinate value. Therefore, so as to attain information necessary for the correction using only the point data, the mesh should be generated and the geometrical information including a plane equation, a normal vector and so on should be used. For this, the 3D coordinate of the tooth configuration is calculated and then the data is expressed as a point group or the mesh according to needs. A technology is developed such that the mesh which displays a surface of the tooth from a huge amount of scanning data in the 3D coordinate form is generated. After an initial triangle is formed by using the point data, a triangular mesh is added by applying a standard of distance·the minimum angle·smoothness.

The outermost edges of the set of triangle generated in this manner share only one triangle. These edges are referred to as boundary edges. A new point is added based on the boundary edges. Lastly, if all the points are used to generate the triangular mesh at least one time, the mesh generating process is finished.

4. Generating a curved surface

All data required for the correction cannot be obtained with only the data in the mesh form. Accordingly, production of a fitted bracket or a prosthesis becomes restricted. This problem can be solved by generating a tooth curved surface equation.

A method for directly generating a curved surface from a polygon has been actively studied and is now on the verge of being commonly used. Quality of the curved surface may be adjusted to a level requested by a user in terms of practical use. Further, according to the method, it is reported that the quality of the curved surface is not quite different according to the user's skill.

It is needed an algorithm in which the polygon is converted into a NURBS (Non Uniform Rational B-Spline) or a trimmed NURBS through a basic technology by generating a general polygon parameter equation and fitting a spatial continuity of curved surfaces on a start point. Here, NURBS is a kind of curved line formed by connecting arbitrary points on the 3D space and is known as one of the most developed forms in curve equations. The NURBS allows the data necessary for the dental correction to be easily extracted from the arbitrary location on the curved surface.

However, if there is no considerable curvature change in data of a surface where a tooth and a tongue are contacted or a surface where a tooth and a lip are contacted among point groups obtained by scanning the tooth according to the present invention, the curved surface may be directly formed by using the point data of wanted portions and then the data necessary for the dental correction may be obtained.

5. Extracting the configuration data

When the prosthesis is installed to correct the tooth to a wanted position, portions supporting the prosthesis in each tooth are adhered. A part connecting the tooth and the prosthesis is called as a bracket. While the bracket produced in large quantities is prevented, the necessary data should be extracted to make correction possible to be made in the optimum way according to tooth of each person.

Accordingly, the following data are extracted to achieve a consistent correction for each patient: an arch form representing the configuration of the overall teeth, a curve equation of a portion on which the bracket is installed, an angulation representing the tilt of the long axis of a tooth in a mesial or distal direction, an inclination representing the tilt of the long axis of a tooth in the buccolingual or faciolingual direction, and an offset representing a distance beyond the arch form on forward and rearward sides.

Here, the angulation angle is an angle tilted rightward and leftward between a perpendicular line and a line connecting the highest point and the lowest point when the front teeth are straightly seen. The inclination angle is an angle between a line perpendicular to an occlusal plane and a tangent line crossing a FA point which is a central point of the teeth, and in other words, an angle tilted between the perpendicular line and the tangent line crossing the central point of the front of the teeth when the each tooth is cut along a direction in which thickness of the teeth becomes thinner. The arch form is a curved line connecting the periphery of the overall teeth. The occlusal plane is a plane including a triangle which connects the highest point of the first tooth and the highest points of the $6^{th}$ teeth on the right and left sides.

Industrial Applicability

As stated above, the present invention has an advantage of easily storing and managing a tooth data by incorporating a tooth plaster model into a computer data base, and easily obtaining a configuration data necessary for tooth correction and tooth implantation. The present invention is applicable to a simulation, such as a virtual correction and a virtual transplantation and also applicable to recovery of a tooth, manufacture of a prosthesis, manufacture of an artificial organ, education and practice.

The present invention has another advantage of helping contribute greatly to the development of technology in medical and rehabilitation fields. Further, the present invention is capable of enabling an accurate medical treatment by providing an accurate 3D data in the dental correction.

The present invention has still another advantage of reducing a time for measuring and extracting a necessary data since it can obtain a wanted data by putting a tooth plaster model on a scanner and performing an input action just a few times with a mouse by a dentist or a dental practitioner.

The present invention further another advantage of reducing a period of time for treating patients and achieving higher reliability from the patients since a prosthesis can be rapidly made according to needs of each patient at a low cost and individual-tailored treatment is ensured.

The present invention has yet another advantage of saving time and money consumed for educating how to use a system or a software by automatizing a lot of parts of a measuring process and of enabling dentists who have no professional knowledge about a machine and a program to easily learn and use the system or the software.

The present invention has yet another advantage of being applicable to a virtual medical treatment, an education, a practice, a simulation, a pronunciation study, and a stress analysis of a tooth and a correcting machine as well as to engineering and manufacturing various medical goods, e.g., an implant, a tooth recovery, a tooth crown, and an operation apparatus.

The forgoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. A 3-dimension scanning system for a computer-aided tooth modeling, the scanning system comprising: image detecting means for extracting an image data of a tooth plaster model; moving means for changing a location and a position of the tooth plaster model measured by the image detecting means; and control means for changing and controlling the location and the position of the tooth plaster model by controlling the moving means to measure the tooth plaster model using the image detecting means;

wherein the control means measures the object by using an automatic teaching method, the teaching method comprising the steps of: simulating a 3-dimension configuration measuring device on a virtual space to determine an order of measuring the tooth plaster model; generating a mesh with respect to a reference tooth model; setting a tooth to be measured; building a reasoning algorithm to automatically determine a measurement angle and a measurement location for the purpose of precisely measuring teeth having different shape and size; incorporating a real measurement result into a database to obtain an accurate measurement path; determining a measurement position including the measurement angle and the measurement location through the reasoning process of the database; measuring the tooth model by using the measurement position and the measurement path; checking whether there exists a portion which is not measured after the above measurement, changing the position of the tooth model and measuring the tooth model again if the unmeasured portion exists, and adding the result to the database.

2. The 3-dimension scanning system of claim 1, wherein the image detecting means comprises: a laser for emitting a laser beam to the tooth plaster model which is an object to be measured; a camera for picking up a reflected beam emitted by the laser; and a video board for grabbing an image signal picked by the camera.

3. The 3-dimension scanning system of claim 1, wherein the moving means comprises: a turn table for allowing the tooth plaster model to be put thereon, and being rotated and tilted to change the location and the position of the tooth plaster model; rotating means for rotating the turn table; tilting means for tilting the turn table; and linear moving means for linearly moving the turn table.

4. The 3-dimension scanning system of claim 1, wherein the control means extracts a configuration data for dental correction by performing the steps of: calculating a 3-dimension coordinate of the tooth configuration and displaying a surface of the tooth by expressing the data into a mesh according to needs; extracting a curved surface data by using the mesh; and extracting the configuration data by using the curved surface data.

5. A 3-dimension scanning method for a computer-aided tooth modelihg, the scanning method comprising the steps of:

(a) installing a tooth model on a base having at least 3-axis rotational degree of freedom, determining an order of scanning a surface of the tooth model and simulating a position where a cross section of a laser emitted onto the surface is minimized;

(b) emitting the laser to the tooth model, scanning and obtaining an image of a laser line;

(c) converting the laser line image into a gray level image and binarizing the same;

(d) finding a center line of the laser line and obtaining a coordinate of the center line;

(e) calculating a 3-dimension coordinate by using the coordinate of the center line and a location of the base;

(f) changing a position of the tooth model by varying the location of the base; and (g) obtaining a 3-dimension coordinate relative to an overall surface of the tooth model by repeating the above steps from (b) to (f);

wherein the tooth model is positioned and located responsive to an automatic teaching method comprising the steps of: simulating a 3-dimension configuration measuring device on a virtual space to determine an order of measuring the tooth model; generating a mesh with respect to a reference tooth model; setting a tooth to be measured; building a reasoning algorithm to automatically determine a measurement angle and a measurement location for the purpose of precisely measuring teeth having different shape and size; incorporating a real measurement result into a database to obtain an accurate measurement path; determining a measurement position including the measurement angle and the measurement location through the reasoning process of the database; measuring the tooth model by using the measurement position and the measurement path; checking whether there exists a portion which is not measured after the above measurement, changing the position of the tooth model and measuring the tooth model again if the unmeasured portion exists, and adding the result to the database.

* * * * *